United States Patent
Dalton et al.

(10) Patent No.: US 8,013,433 B2
(45) Date of Patent: Sep. 6, 2011

(54) VIRTUAL WIRE ASSEMBLY HAVING HERMETIC FEEDTHROUGHS

(75) Inventors: James Dalton, Beecroft (AU); Peter Single, Lane Cove (AU); David Money, Pennant Hills (AU)

(73) Assignee: Cochlear Limited, Macquarie University, NSW ( * ) Notice: Subject to any disclaimer, the term of this patent is extended or adjusted under 35 U.S.C. 154(b) by 1285 days.

(21) Appl. No.: 11/647,208

(22) Filed: Dec. 29, 2006

(65) Prior Publication Data

US 2007/0112396 A1   May 17, 2007

Related U.S. Application Data

(63) Continuation of application No. 10/798,847, filed on Mar. 12, 2004, now Pat. No. 7,174,223.

(30) Foreign Application Priority Data

Mar. 12, 2003   (AU) ................ 2003901146

(51) Int. Cl.
*H01L 23/04* (2006.01)
*H01L 23/053* (2006.01)
*H01L 23/12* (2006.01)
*H01L 23/48* (2006.01)
*H01L 23/52* (2006.01)
*H01L 29/40* (2006.01)

(52) U.S. Cl. ........ 257/698; 257/699; 257/700; 257/774; 257/E23.011; 257/E23.067; 257/E23.147; 257/E23.174

(58) Field of Classification Search .......... 257/700, 257/774, E23.011, E23.067, E23.145, E23.174, 257/698–699
See application file for complete search history.

(56) References Cited

U.S. PATENT DOCUMENTS

| | | | | |
|---|---|---|---|---|
| 3,683,245 A | * | 8/1972 | Bacher et al. | 361/304 |
| 4,001,586 A | * | 1/1977 | Fraioli | 250/345 |
| 4,151,479 A | * | 4/1979 | Baba | 330/264 |
| 4,208,698 A | * | 6/1980 | Narasimhan | 361/793 |
| 4,650,285 A | * | 3/1987 | Stevenson | 250/227.11 |
| 4,746,893 A | * | 5/1988 | Shak | 338/5 |
| 4,861,944 A | * | 8/1989 | Jones et al. | 174/262 |
| 4,866,571 A | * | 9/1989 | Butt | 361/717 |
| 5,046,242 A | | 9/1991 | Kuzma | |
| 5,166,773 A | * | 11/1992 | Temple et al. | 257/678 |
| 5,229,549 A | * | 7/1993 | Yamakawa et al. | 174/262 |
| 5,241,456 A | * | 8/1993 | Marcinkiewicz et al. | 361/792 |
| 5,315,486 A | * | 5/1994 | Fillion et al. | 361/792 |
| 5,331,203 A | * | 7/1994 | Wojnarowski et al. | 257/698 |
| 5,359,496 A | * | 10/1994 | Kornrumpf et al. | 361/795 |
| 5,371,321 A | * | 12/1994 | Hamzehdoost et al. | 174/551 |
| 5,412,748 A | | 5/1995 | Furuyama et al. | |
| 5,446,316 A | * | 8/1995 | Temple et al. | 257/704 |
| 5,448,014 A | * | 9/1995 | Kong et al. | 174/539 |
| 5,454,161 A | * | 10/1995 | Beilin et al. | 29/852 |
| 5,637,920 A | * | 6/1997 | Loo | 257/700 |
| 5,712,768 A | * | 1/1998 | Werther | 361/767 |

(Continued)

*Primary Examiner* — Ida M Soward
(74) *Attorney, Agent, or Firm* — Kilpatrick Townsend & Stockton LLP

(57) ABSTRACT

A virtual wire assembly that includes a substantially electrically-nonconductive substrate and a plurality of hermetic feedthroughs including a conductive region extending transversely through the substrate to form a conductive pathway with accessible surfaces at opposing ends thereof, wherein each conductive pathway is electrically isolated from other conductive pathways. In certain embodiments of this aspect of the invention, the substantially electrically-nonconductive substrate is a semiconductor device, and the conductive regions each include an n-type or a p-type doped semiconductor material.

30 Claims, 6 Drawing Sheets

U.S. PATENT DOCUMENTS

| | | | |
|---|---|---|---|
| 5,723,904 A * | 3/1998 | Shiga | 257/698 |
| 5,734,560 A * | 3/1998 | Kamperman et al. | 361/774 |
| 5,747,169 A * | 5/1998 | Fan et al. | 428/426 |
| 5,770,476 A * | 6/1998 | Stone | 438/106 |
| 5,814,883 A * | 9/1998 | Sawai et al. | 257/712 |
| 5,837,356 A * | 11/1998 | Katori et al. | 428/210 |
| 6,201,300 B1 * | 3/2001 | Tseng et al. | 257/706 |
| 6,230,057 B1 | 5/2001 | Chow et al. | |
| 6,321,126 B1 | 11/2001 | Kuzma | |
| 6,383,835 B1 * | 5/2002 | Hata et al. | 438/65 |
| 6,501,170 B1 | 12/2002 | Dickey et al. | |
| 6,501,340 B1 * | 12/2002 | Flood | 331/69 |
| 6,517,362 B2 * | 2/2003 | Hirai et al. | 439/82 |
| 6,583,058 B1 * | 6/2003 | Rajendran et al. | 438/675 |
| 6,777,612 B2 * | 8/2004 | Sugiura et al. | 174/539 |
| 6,778,040 B2 | 8/2004 | Kim | |
| 7,535,093 B1 * | 5/2009 | Ables et al. | 257/698 |
| 2001/0050837 A1 | 12/2001 | Stevenson et al. | |
| 2002/0139556 A1 * | 10/2002 | Ok et al. | 174/50.6 |
| 2003/0062969 A1 * | 4/2003 | Inoue | 333/193 |
| 2003/0109903 A1 | 6/2003 | Berrang et al. | |
| 2003/0233133 A1 | 12/2003 | Greenberg et al. | |
| 2004/0147992 A1 | 7/2004 | Bluger et al. | |
| 2005/0146039 A1 * | 7/2005 | Shah et al. | 257/758 |

* cited by examiner

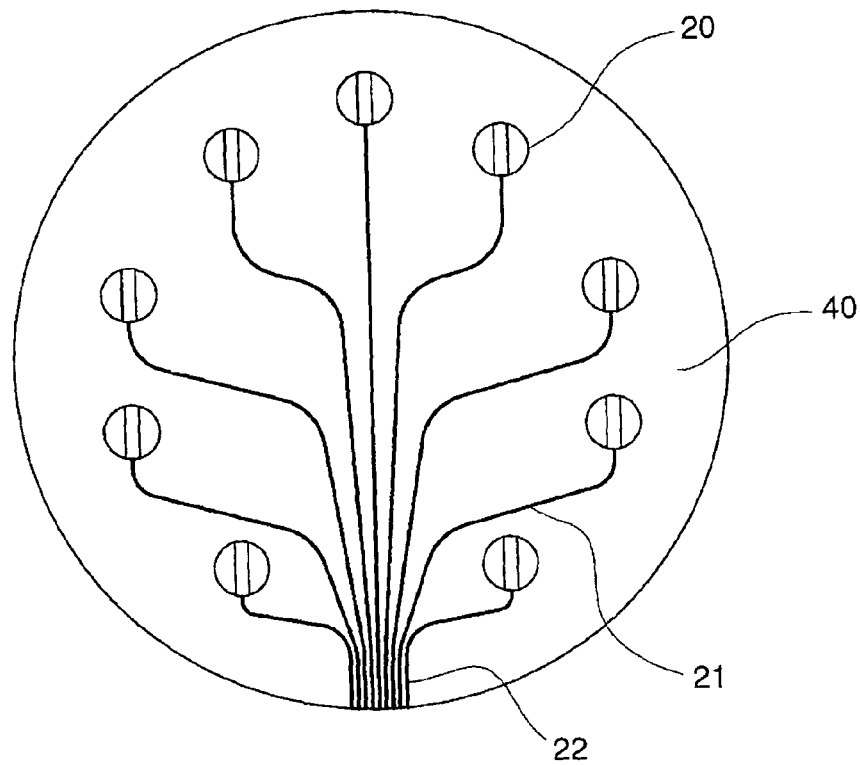
Fig.4
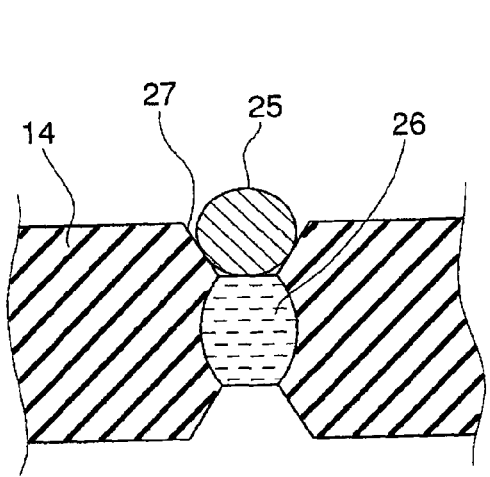
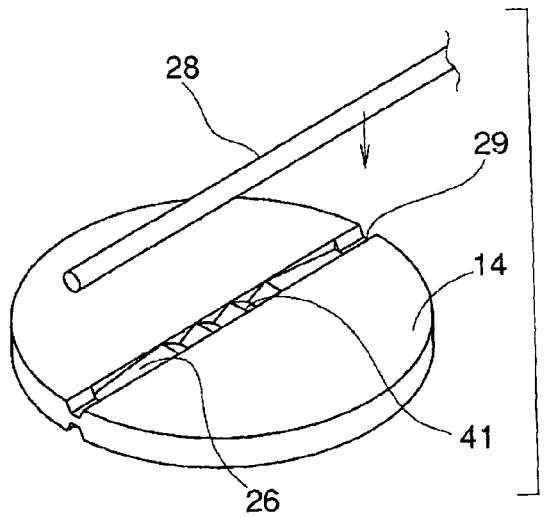
Fig.5A    Fig.5B

VIRTUAL WIRE ASSEMBLY HAVING HERMETIC FEEDTHROUGHS

CROSS-REFERENCE TO RELATED APPLICATIONS

This application is a continuation of U.S. patent application Ser. No. 10/798,847 filed on Mar. 12, 2004, entitled, "Virtual Wire Assembly Having Hermetic Feedthroughs,", now issued on Feb. 6, 2007 as U.S. Pat. No. 7,174,223, which claims priority to Australian Provisional Patent Application No. 20039001146, entitled "Feedthrough Assembly," filed on Mar. 12, 2003. The entire disclosure and contents of the above applications are hereby incorporated by reference.

BACKGROUND

1. Field of the Invention

The present invention relates to feedthrough devices.

2. Related Art

Historically, feedthrough devices were widely used in vacuum technology allowing for the transfer of signals between chambers of differing pressures. In such applications, the vacuum tubes had to be sealed because they could only operate under low pressure conditions. In the early feedthrough devices, such as those used for vacuum tubes, the feedthroughs were essentially made from glass plugs which were partly melted to allow electrical conductors to be passed therethrough.

Over time, other devices have also required a mechanism of allowing electrical connections between hermetically sealed circuitry and an external device, such as those devices that are used in medical implants to provide therapy to a patient, such as cardiac pacemakers, defibrillators and cochlear implants. As the environment of living tissue and body fluids is quite corrosive and the implants may contain materials which may be detrimental to the patient, a hermetic feedthrough device is used to provide a barrier between the devices electronics and the external corrosive environment of the human body.

One example of a feedthrough developed for use in medical devices is shown in U.S. Pat. No. 4,678,868. The '868 patent describes an alumina insulator to provide hermetic sealing and electrical isolation of a niobium conductor pin from a metal case. Other typical feedthrough devices utilize a conductive pin to provide a conductive path through the feedthrough and also include a ferrule which permits attachment of the feedthrough to the case. The conductive pin and a hermetic glass or ceramic seal which supports the pin within the ferrule and isolates the pin from the metal casing. However, these types of feedthroughs have generally been not acceptable for use in medical implant applications because of the likelihood of corrosion and deterioration.

Other materials and processes are known for making feedthroughs, for example, from aluminum oxide ceramic and binders. These types of feedthroughs are widely used for cardiac and cochlear implants. One of the processes for making such a feedthrough consists of pre-drilling holes in a sintered ceramic plate and then forcing electrical conductive pins through the holes. However, this method does not necessarily guarantee a hermetic seal. A second method involves inserting the conductive pins into an unsintered (or "green") ceramic plate and then curing the assembly by firing to achieve a hermetic seal. A major disadvantage of this last method is that, historically this has been performed by hand. Such a method of manufacture can lead to inaccuracies and be time consuming, expensive and labor intensive. Moreover, the feedthrough devices resulting from such a process do not necessarily have precisely positioned electrical conductors. The position of the conductors being greatly dependent upon the process itself.

SUMMARY

In one aspect of the invention, a virtual wire assembly is disclosed. The assembly comprises: a substantially electrically-nonconductive substrate; and a plurality of hermetic feedthroughs each comprising a conductive region extending substantially transversely through the substrate to form a conductive pathway with accessible surfaces at opposing ends thereof, wherein each conductive pathway is electrically isolated from other conductive pathways. In certain embodiments of this aspect of the invention, the substantially electrically-nonconductive substrate is a semiconductor device, and the conductive regions each are comprised of an n-type or a p-type doped semiconductor material.

In another aspect of the invention, a cochlear prosthesis is disclosed. The prosthesis comprises an external control unit that determines a pattern of electrical stimulation; and an implanted stimulator unit operationally coupled to the control unit and comprising circuitry housed in a hermetic enclosure comprising a casing and a virtual wire assembly hermetically sealed within an aperture of the casing and having hermetic feedthroughs through which electrical stimulation channels are routed to provide electrical stimulation of auditory nerve cells. In certain embodiments of this aspect of the invention, the virtual wire assembly comprises: a substantially electrically-nonconductive substrate hermetically sealed within an aperture of the casing; and the hermetic feedthroughs, wherein the hermetic feedthroughs each comprise a conductive region extending substantially transversely through the substrate to form a conductive pathway with accessible surfaces at opposing ends thereof, wherein each conductive pathway is electrically isolated from other conductive pathways.

In a further aspect of the invention, a method is disclosed. The method comprises: providing a substantially electrically-nonconductive substrate; and forming through the substrate a plurality of permanent hermetic feedthroughs each comprising a conductive region extending substantially transversely through the substrate to form a conductive pathway with accessible surfaces at opposing ends thereof, wherein each conductive pathway is electrically isolated from other conductive pathways. In one particular embodiment of this aspect of the invention, providing a substantially electrically-nonconductive substrate comprises providing a semiconductor device, and wherein forming a plurality of conductive, and wherein forming a plurality of permanent hermetic feedthroughs through the substrate comprises doping the substrate to form n-type or p-type doped regions extending transversely through the substrate.

In a still further aspect of the invention, an implantable medical device is disclosed. The device comprises circuitry; and a hermetic enclosure in which the circuitry is housed, the hermetic enclosure comprising a casing with an aperture; and a virtual wire assembly hermetically sealed within the aperture of the casing and having hermetic feedthroughs through which electrical signals can be routed. In one particular embodiment of this aspect of the invention, the virtual wire assembly comprises: a substantially electrically-nonconductive substrate hermetically sealed within an aperture of the casing; and the hermetic feedthroughs, wherein the hermetic feedthroughs each comprise a conductive region extending substantially transversely through the substrate to form a conductive pathway with accessible surfaces at opposing ends thereof, wherein each conductive pathway is electrically isolated from other conductive pathways.

BRIEF DESCRIPTION OF THE DRAWINGS

The invention will be described in conjunction with the accompanying drawings, in which:

FIG. 4 is a plan view of a substrate with a plurality electrical leads in position in accordance with one embodiment of present invention;

FIG. 5A is a cross-sectional view of a conductive region attached a wire within a groove in the substrate in accordance with one embodiment of present invention;

FIG. 5B is a perspective view of a grooved recess, having teeth, formed in the surface of a substrate and an electrical lead for mounting in this groove in accordance with one embodiment of present invention;

DETAILED DESCRIPTION

Embodiments of the present invention are directed to a virtual wire assembly that provides hermetic feedthroughs which can be used, for example, in devices requiring electronic or other components to be retained in an impermeable enclosure. Such devices include, for example, fully- or partially-implanted medical devices that interface with biological systems. Examples of such medical devices include, but are not limited to, sensory prosthetic devices and neural prosthetic devices. In sensory prostheses, information is collected by electronic sensors and delivered directly to the nervous system by electrical stimulation of pathways in or leading to the parts of the brain that normally process a given sensory modality. Neural prostheses are clinical applications of neural control interfaces whereby information is exchanged between neural and electronic circuits.

Embodiments of the present invention are described below in connection with one type of medical device, a cochlear prosthetic device. Cochlear prostheses use direct electrical stimulation of auditory nerve cells to bypass absent or defective hair cells that normally transducer acoustic vibrations into neural activity. Such devices generally use multi-contact electrodes inserted into the scala tympani of the cochlea so that they can differentially activate auditory neurons that normally encode differential pitches of sound. A smaller number of patients with bilateral degeneration of the auditory nerve have been treated with modest success by stimulation of the cochlear nucleus in the brainstem. Cochlear prostheses such as that described in U.S. Pat. Nos. 6,537,200 and 6,697,674, the entire contents and disclosures of which are hereby incorporated by reference, generally include an external, wearable control unit that determines a pattern of electrical stimulation that is provided to an implanted stimulator unit containing active circuitry in a hermetic enclosure. Electrical stimulation channels are routed through feedthroughs of the stimulator to provide electrical stimulation of auditory nerve cells.

Figure 1:
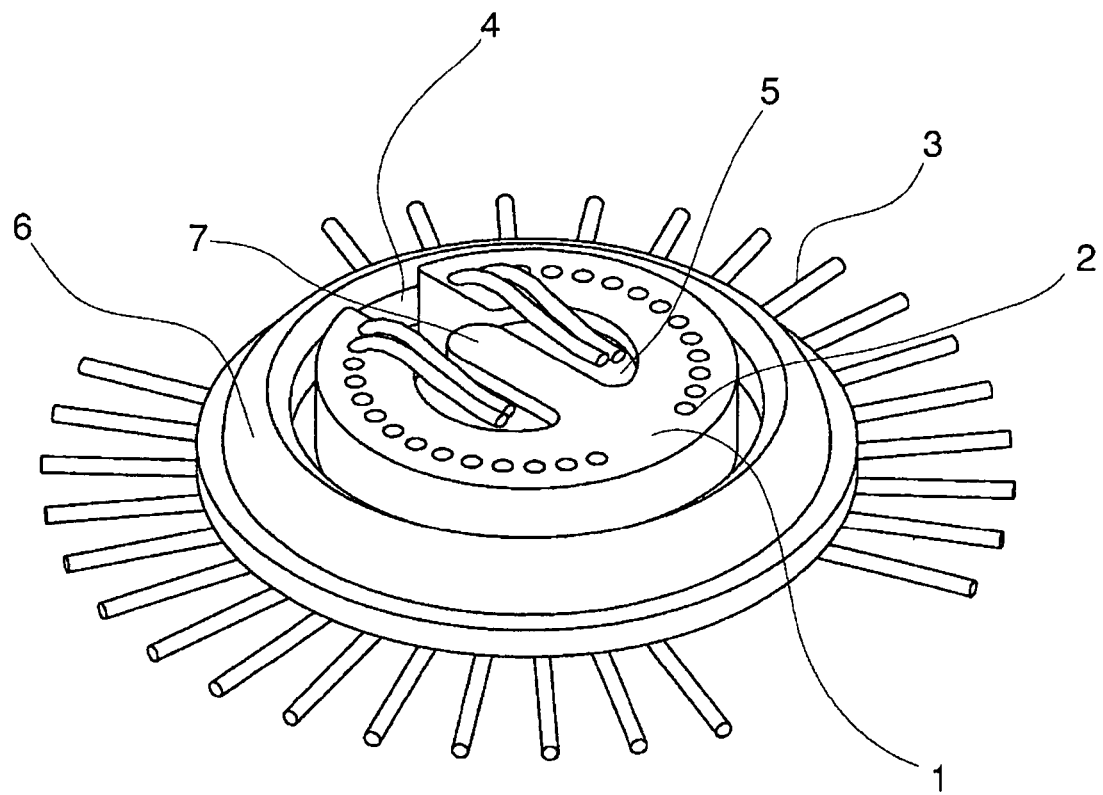
FIG. 1 is a perspective view of a prior art feedthrough assembly.

An example of a prior art ceramic feedthrough assembly for a cochlear implant is shown in FIG. 1. A ceramic disc 1 is machined to about 10 mm in diameter and 2 mm in thickness, and has twenty-eight individual holes 2, punched therethrough to accommodate each of the connector pins 3 (shown unconnected in FIG. 1). Following insertion of each connector pin 3 into each respective hole 2, ceramic disc 1 is further machined to provide grooves 4. Ceramic disc 1 is then sintered to provide hermeticity to the entire assembly.

Following sintering, two titanium pads 5 are spot welded into grooves 4 and a flange 6 is positioned and brazed around the entire assembly. Pins 3 are then dipped into a molten solder bath to ensure an even coating of solder and then formed into the radial position as shown in FIG. 1. The heads of pins 3 adjacent to the outer surface 7 are attached to wires (not shown) that are connected to electrodes (also not shown) which are in turn inserted into the cochlea of a patient to provide audible stimulation. The attachment of the pins 3 to the electrode wires is achieved by etching a V-shaped groove onto the surface of each pinhead and crimping and soldering the wire in place. The pins adjacent the inner surface of the device are attached to the internal circuitry via conventional soldering techniques.

As illustrated in FIG. 1, the conventional feedthrough assembly is a complicated device requiring a number of components carefully pieced together. The manufacturing process for such prior art feedthrough assemblies is both complicated and time consuming, and requires much skill and effort to produce a device of sufficient quality and reliability.

With the increase in the number of leads used for stimulation and sensory purposes in medical implant applications, the feedthrough requirements of implantable medical devices have also increased. For example, modern cochlear prostheses often have implanted stimulator unit that drives 22-24 channels requiring a corresponding quantity of dedicated electrode leads and, therefore, conductive pins passing through the feedthrough device. The problems in fabricating such feedthrough devices on a large scale are therefore quite significant, especially when one considers the relatively high degree of labor intensity and specialization of the current fabricating methods.

Figures 2A, 2B:
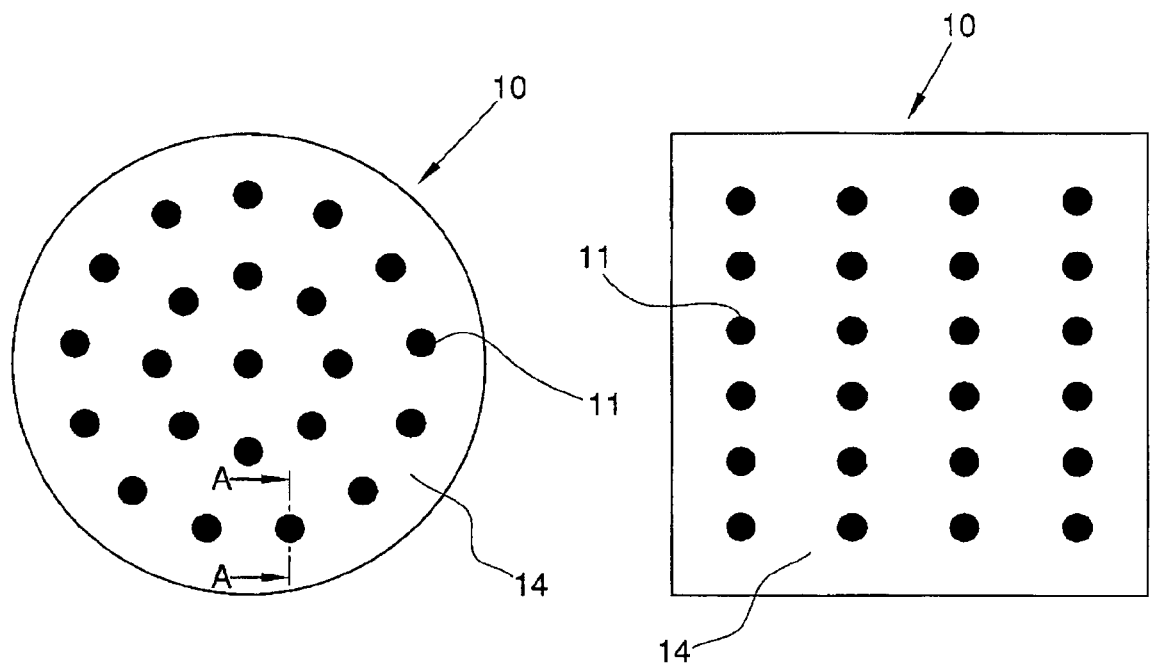
FIGS. 2A and 2B are each plan views of a substrate having a plurality of localized conductive regions for use as conductive pathways in accordance with an embodiment of the present invention.

FIGS. 2A and 2B are a top perspective view of one embodiment of a virtual wire assembly 10 of the present invention that includes wireless hermetic feedthroughs or conductive paths 11 that extend through a substrate 14. Virtual wire assembly 10 may be used, for example, in implanted medical devices including sensory prosthetic devices such as cochlear implants. In such an application, virtual wire assembly 10 provides a plurality of wireless hermetic feedthroughs or conductive paths 11 to electrically connect active microelectronics disposed in the implanted component to maintain the circuitry in an impermeable enclosure. Thus, conductive paths 11 conduct electrical signals across an enclosure wall while at the same time preventing the passage of any gases or liquids into the enclosure. This is described in further detail below.

Figures 3A, 3B:
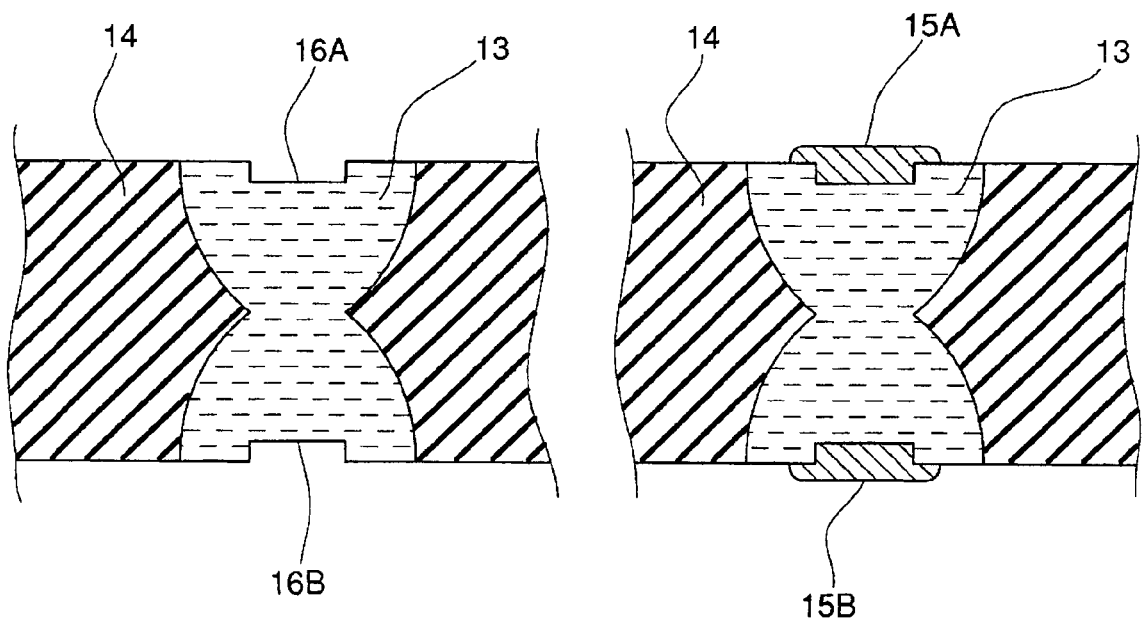
FIG. 3A is a partial cross-sectional view of a conductive region with grooves in accordance with one embodiment of present invention.
FIG. 3B is a partial cross-sectional view of a conductive region with a pair of deposited terminals in accordance with one embodiment of present invention.

FIG. 3A shows a cross-sectional view of a portion of virtual wire assembly 10 in FIG. 2A taken through one conductive path 11 as shown by the line A-A'. Virtual wire assembly 10 comprises a substrate 14 that is substantially electrically non-conductive. Disposed in substrate 14 is a plurality of conductive regions 13 each forming a wireless, hermetic conductive path 11 through the substrate. Each conductive path 11 is isolated from the other conductive paths 11; that is, each conductive path 11 is localized.

Each conductive path 11 extends transversely through substrate 14 so as to be accessible from each side of the substrate to facilitate electrical communication through the substrate via conductive path 11. In one embodiment of the present invention, substrate 14 is a semiconductor device made, for example, from silicon. Semiconductor device 14 is doped to form n-type or p-type conductive regions 13. To ensure conductive region 13 extends completely through the full thickness of substrate 14, the doping may be done on both sides of the substrate. Conductive regions 13 may have any dimensions suitable for a particular application, and as shown in FIGS. 3A and 3B, may have cross-sectional dimensions that vary along the longitudinal axis of the conductive regions 13.

As noted, opposing ends of each conductive region 13 are accessible at each side of substrate 14. Each side of conductive region 13 is in electrical communication with an electrical contact, such as a terminal, pad or wire, to form a conductive pathway or virtual connector pin that eliminates the need for drilling and insertion of physical pins, and that eliminates the subsequent problems associated with ensuring hermeticity. Each conductive pathway is, as noted, formed to ensure that conductive pathway is localized with respect to the other conductive pathways on the substrate.

Electrical contacts are placed on each end of conductive path 11 to facilitate electrical communication with another component as described below. In the embodiment shown in FIG. 3A, the electrical contacts are implemented as a notched or grooved surface at the exposed end of conductive region 13. Grooves 16A, 16B in conductive region 13 which allow for a wire or other electrical contacting means to be in electrical communication.

In an alternative embodiment such as that shown in FIG. 3B, interconnect terminals 15A, 15B are connected to the exposed ends of conductive path 11. Thus, in the embodiments shown in FIGS. 3A and 3B, conductive paths 11 each extend through substrate 14 and have electrical contacts on opposing ends of conductive path 11 which are exposed at the opposing surfaces of substrate 14.

It should be understood that the longitudinal axis of each conductive region 13 may each extend substantially orthogonal or diagonal to the plane of the surface of substrate 14. Similarly, conductive regions 13 may or may not be substantially parallel with each other. It should also be appreciated that different embodiments of virtual wire assembly 10 can have different cross-sectional dimensions. As can be seen in FIGS. 2A and 2B, virtual wire assembly 10 may be in any desired form, from a substantially circular shape as shown in FIG. 2A to a substantially square or rectangular shape as shown in FIG. 2B. It should be obvious to one of ordinary skill in the art that other cross-sectional shapes of a virtual wire assembly may be envisaged by the present invention.

In the exemplary application of a cochlear implant, the surface of virtual wire assembly 10 is substantially planar. However, as one of ordinary skill in the art would appreciate, the exterior surface of virtual wire assembly 10 can be concave, convex or any contoured or variable surface suitable for a particular application.

Referring now to FIG. 3B, interconnect terminals 15A, 15B are formed by depositing a conductive pad on the surface of a conductive region 13 which may extend substantially transversely through substrate 14. Each terminal 15 is formed of at least one conductive material, such as platinum, gold, or a eutectic alloy, that is suitable for a biological implant. Terminal 15 is formed to aid in the attachment of wires (not shown) on either surface of virtual wire assembly 10.

In addition, it should be obvious to one of ordinary skill in the art that the pair of electrical contacts do not need to be the same type of contacts on each side of a conductive region 13. For example, depending on the application, it made be necessary have a terminal attached to a wire on one side of a conductive region 13 and a groove for inserting a wire on the other side of the same conductive region 13. Nor are all the conductive regions 13 in an embodiment of virtual wire assembly 10 required to have the same type of contact or the same or opposing ends of conductive region 13.

The number of conductive pathways may vary depending on the application with which a virtual wire assembly of the present invention is being used. For example, a virtual wire assembly used in a implanted stimulator unit of a cochlear prosthesis may require at least twenty-two conductive paths to allow for connection of twenty-two stimulating electrodes to the implant circuitry. Other applications may not require as many, or more, paths, however. It is an advantage of the present invention that virtual wire assemblies may be made and customized to suit differing requirements with minimal changes in the manufacturing methods. An advantage of certain embodiments of the present invention is that an increase of conductive pathways does not increase the labor associated number of holes that are required to be sealed.

A substrate of the present invention may comprise an electrically insulating material having a first surface and a second surface. The substrate has at least one transverse intrinsic region extending through the substrate between the first surface and the second surface that is electrically conducting relative to the electrical conductivity of the substrate.

As noted, in one embodiment, substrate may be rendered at least relatively electrically semiconducting in discrete regions, i.e., conductive regions. In another embodiment of the present invention, a substrate may comprise a semiconducting crystalline material such as a silicon wafer. Substrate may also be made of other materials, such as high density silicon, germanium and gallium arsenide.

The transverse conductive region may comprise a region of n-type or p-type semiconductor material formed by appropriate doping of the substrate with a suitable impurity in the region. In a preferred embodiment of the present invention, the doping may occur at both the first and second surfaces to ensure that the low impedance electrically conducting region extends through the substrate.

It should be appreciated from the above that each conductive pathway acts as a "virtual wire" that preferably eliminates the need for drilling and insertion of physical pins, and the subsequent problems associated with ensuring hermeticity. Certain embodiments of the present invention also provide a virtual wire that is advantageous over the conventional because no pin is fed through a hole in the device, rather conductive pathways without holes act as pins. This may decrease the likelihood of deterioration of the device when used in medical implant applications. In addition, an advantage of certain embodiments of the present invention is that the use of virtual wire allows a greater density of conductive pathways to be placed onto a substrate without increasing the need for more hermetical seals. A further advantage of some embodiments of the present invention is that they allow for the precise positioning of the electrical contacts by arrangement of conductive pathways.

Figure 7:
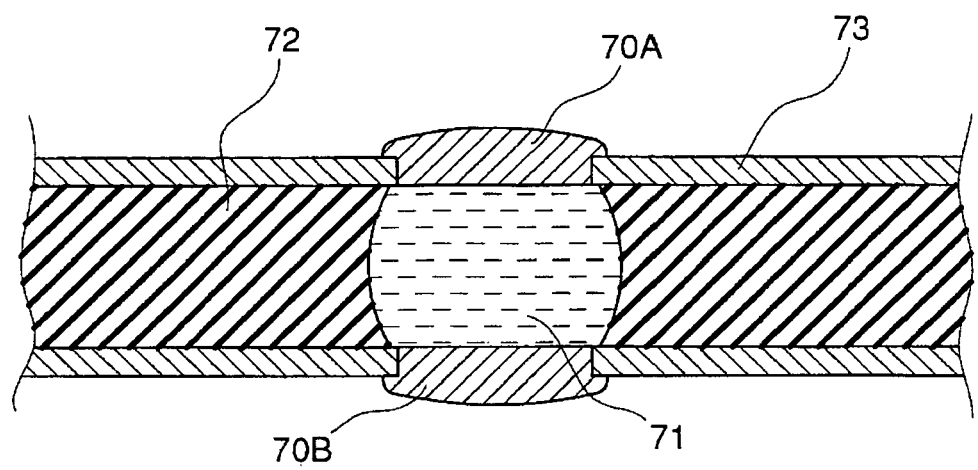
FIG. 7 is a cross-sectional view of a conductive region with a pair of pads in accordance with one embodiment of present invention.

FIG. 7 is a cross-sectional view of a conductive region and associated contacts in accordance with an alternative embodiment of the present invention. A conductive region 71 is disposed in substrate 72. In this embodiment, electrical contacts connected to opposing ends conductive region 71 are conductive pads 70A, 70B. Pad 70 is in the form of a conductive metal pad and is deposited to cover the entire exposed surface of conductive region 71 formed in substrate 72. In this example, substrate 72 is provided with an additional deposited layer 73, such as silicon dioxide, $SiO_2$+SiN P Glass or B Glass in order to control the surface of the high density silicon substrate.

A virtual wire assembly 40 of the present invention may be arranged as shown in FIG. 4. Each conductive region 20 of virtual wire assembly 40 is connected by a wire 21 which in turn is connected to a device such as a circuit board or a stimulating electrode. Wires 21 may be bundled together in a common bundle 22 and branched off to singly connect to one surface of a conductive region 20.

Mounting of the electrically conductive wires 21 may be achieved through a number of bonding means, including soldering, gap welding, wirebonding and electrically conductive epoxies. Mechanical bonding techniques, such as crimping, can also be envisaged by the present invention. In some embodiments, wires 21 may be deposited by such techniques a chemical vapor deposition.

Two examples of such mechanical means will be described below and are shown in FIGS. 5A and 5B. FIG. 5A shows one particular method of attaching a wire 25 to a corresponding conductive region 26. As can be seen, a depression 27 is formed on the surface of substrate 14 above conductive region 26 and wire 25 is then forced into depression 27 and bonded in place by a suitable "cold weld" method. By the term "cold weld" it is meant to incorporate any method of welding the wire to the silicon surface under high pressure or vacuum without the use of heat. This method of attachment does not require any soldering or welding and utilizes physical forces to maintain the wire in place. The other end of wire 25 could then be attached to a circuit board or electrode or any other suitable device depending upon the desired application.

FIG. 5B shows another similar type method of attaching a wire 28 to a corresponding conductive region 26 of a virtual wire assembly in accordance with an embodiment of the present invention. A depression 29 is formed in substrate 14 above a conductive region 26 in much the same way as in FIG. 5A. Wire 28 is held under tension and compressed into depression 29 until it is engaged with teeth 41. The tension forces acting upon wire 28 force wire 28 into engagement resulting in an attachment that is purely mechanical and which does not require welding or the like.

It should be obvious to one of ordinary skill in the art that electrical contacts in addition to wires may be placed in the depressions, such as terminals and pads.

Following the attachment of wires to both sides of a conductive region and completing the conductive pathway across the substrate, the virtual wire assembly is sealed so that hermeticity is maintained. Such a method of sealing is shown for example in FIG. 6.

Figure 6:
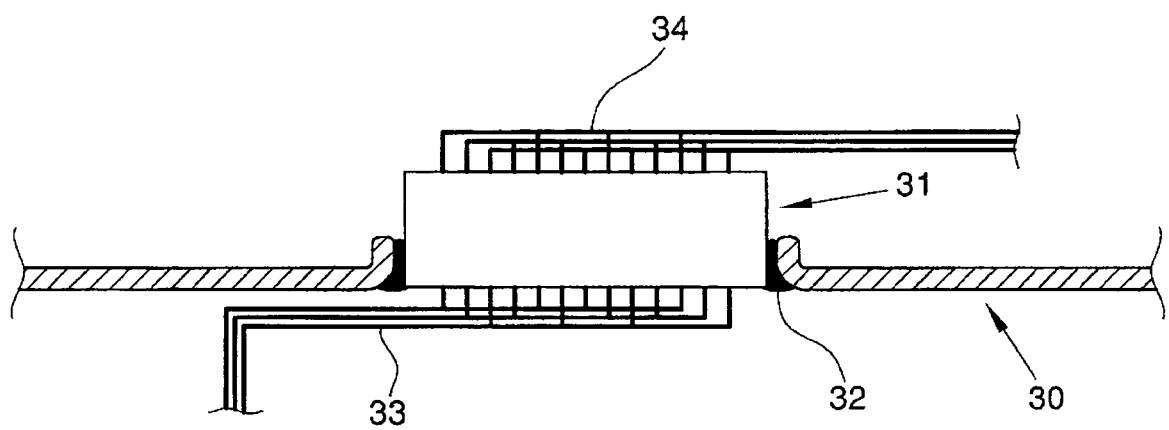
FIG. 6 is a side elevation view of a substrate mounted in a hermetically sealed case in accordance with one embodiment of present invention.

FIG. 6 shows a virtual wire assembly 31 positioned within a wall of a casing 30 of a device, for example the casing of an implanted stimulator unit such as those used in cochlear implants, pacemakers and the like. Casing 30 may be made of titanium forming a hermetic shell around the implanted stimulator unit isolating the internal circuitry and the like from the body fluids with which the unit is implanted. Virtual wire assembly 31 has wires 33 attached to one side thereof, this side being enclosed by the titanium shell and being connected to the internal circuitry of the implanted stimulator unit. There are also corresponding wires 34 attached to the external surface of virtual wire assembly 31 which are connected to stimulating electrodes or the like (not shown) allowing the internal circuitry of the implanted stimulator unit to communicate directly with the stimulating electrodes or the like via virtual wire assembly 31. In order to maintain a hermetic seal between the internal implanted circuitry and the environment of living tissue and body fluids, virtual wire assembly 31 is sealingly connected to casing 30 of the implanted stimulator unit by means of a suitable weld or braze 32. Braze 32 must be suitable to ensure a hermetic seal around virtual wire assembly 31. As one of ordinary skill in the art would find apparent, a virtual wire assembly of the present invention may be attached to the casing in a number of arrangements, depending on the function of the overall device.

Figure 8:
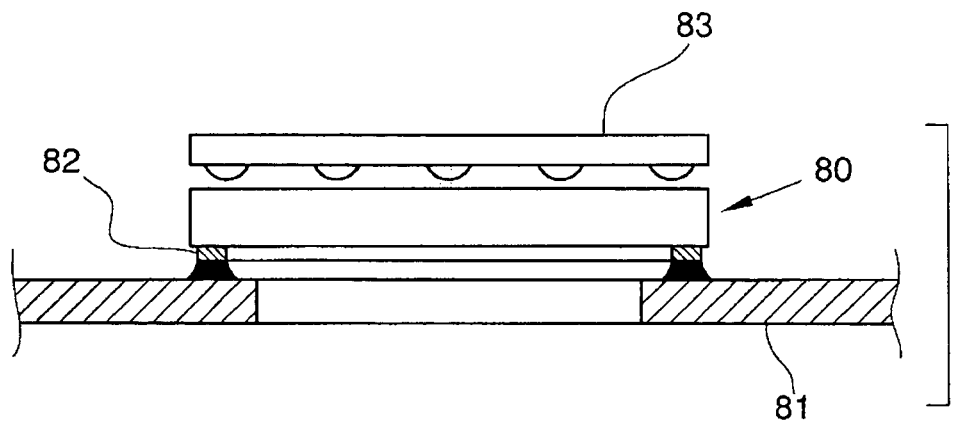
FIG. 8 is a cross-sectional view of substrate mounted in a hermetically sealed case and attached to a ball grid array in accordance with one embodiment of present invention.

FIG. 8 shows an arrangement, in which one side of a virtual wire assembly 80 is connected to a ball grid array 83 to form a face joint. Virtual wire assembly 80 is also joined to a casing 81 with a metallic annulus 82 bonded to virtual wire assembly 80. Metallic annulus 82 is then brazed to casing 81. Casing 81 is formed from any suitable material such as titanium.

Figure 9:
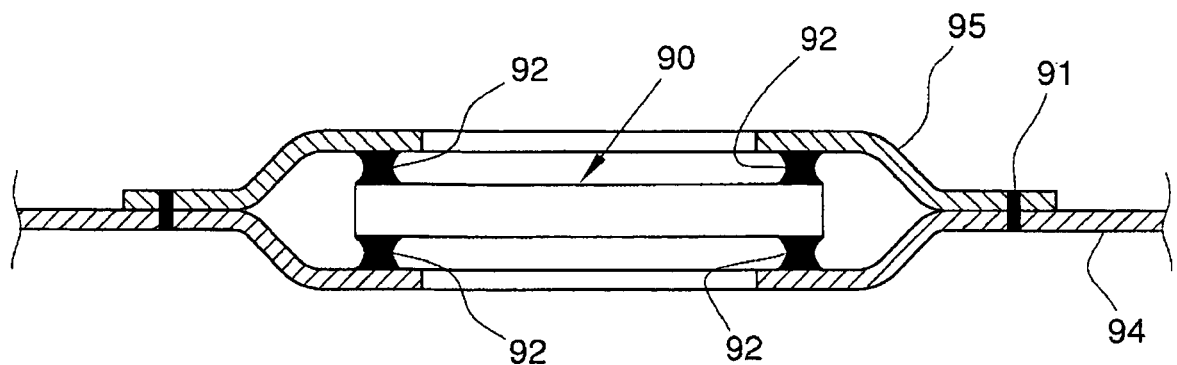
FIG. 9 is a cross-sectional view of substrate mounted in hermetically sealed case using a dual face joint in accordance with one embodiment of present invention.

FIG. 9 shows yet another arrangement, in which a virtual wire assembly 90 uses a dual face joint to casing 94. Virtual wire assembly 90 is provided with a braze 92 on opposing sides. One side is bonded to casing 94 and the other side is bonded to an upper casing extension 95. A laser weld 91 is used to adhere upper casing extension 95 to casing 94. This arrangement provides stiffness around virtual wire assembly 90, thus providing protection against bending moments.

Figure 10:
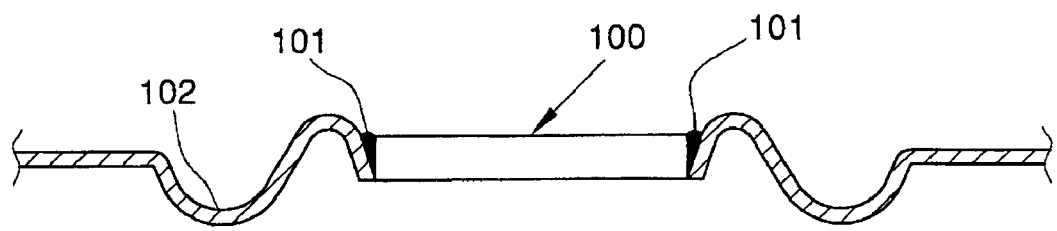
FIG. 10 is a cross-sectional view of substrate mounted in a hermetically sealed case using a joints in accordance with one embodiment of present invention.

Another variation for mounting a virtual wire assembly 100 is shown in FIG. 10. At a joint 101 virtual wire assembly 100 is attached to casing 102. Casing 102 is corrugated to avoid virtual wire assembly 100 from being bent.

Figure 11:
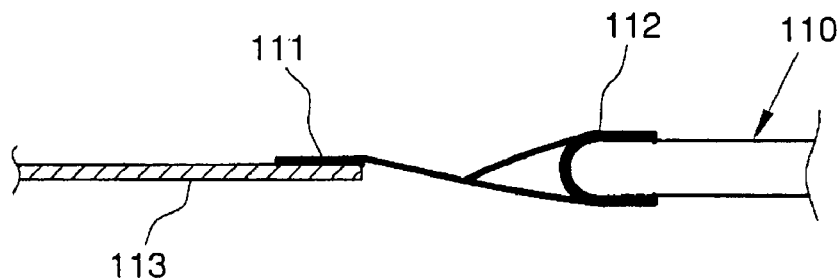
FIG. 11 is a detail view of a substrate connected to a hermetically sealed case in accordance with one embodiment of present invention.

Another arrangement is shown in FIG. 11, where virtual wire assembly 110 is plated at one end 112 and welded at one end 111 of a casing 113. A similar arrangement may be used to attached the other end of the virtual wire assembly 110 to casing 113.

Figure 12:
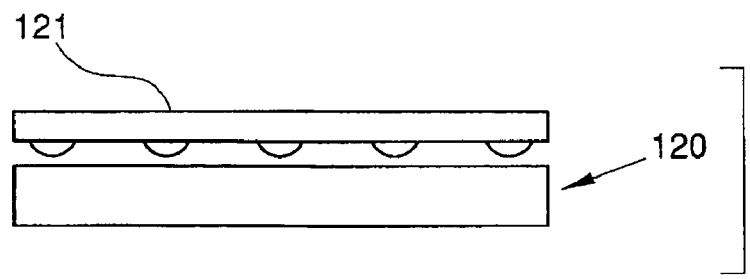
FIG. 12 is a cross-sectional view of a ball grid array interface with a substrate in accordance with one embodiment of present invention.

FIG. 12 shows a set of contacts comprising a ball grid array 121 in contact with a virtual wire assembly 120 of the present invention.

Figure 13:
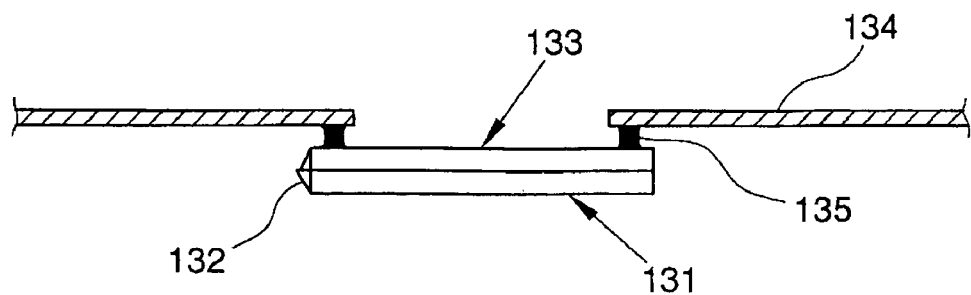
FIG. 13 is a cross-sectional view of a separable interface between two virtual wire assemblies in accordance with one embodiment of present invention.

FIG. 13 depicts a separable connection between a top virtual wire assembly 133 and a bottom virtual wire assembly 131. Bottom feedthrough assembly 131 is mated at mating region 132 so that the conductive pathways are substantial aligned with top virtual wire assembly 133. Top virtual wire assembly 133 is attached to casing 134 to form a hermetic enclosure using a weld/braze 135 as previously described above. Typically, bottom virtual wire assembly 131 is attached to an additional, discrete hermetic enclosure or other component, so as to enable the separation of one assembly does not dislodge or remove the other. The surface finish of the mating faces is such that conductivity is possible across the interface between bottom virtual wire assembly 131 and top virtual wire assembly 133. Body fluid ingress is not possible between the two faces. In a preferred embodiment, a micromachined joint aligns the two devices and secures them in close contact.

The overall thickness of the substrate may be determined by the application with which a virtual wire assembly of the present invention is to be used. In addition, the overall thickness of the substrate may be determined by the limitations of conventional doping processes.

An electrical contact of the present invention, such as a terminal, pad, naked wire, etc., may also be formed from an organic polymeric material that is normally electrically insulating but which can be rendered relatively electrically conducting by exposure to a weak oxidation agent, such as Iodine, Arsenic Pentachloride, Iron (III) Chloride or $NOPF_6$, or a reducing agent, such as sodium naphthalide, which act as a dopant. Intrinsically electrically conducting polymers, such as polyheterocyclics like polypyrrole, polythiophene and their derivatives, also are encompassed within the scope of the invention.

In another embodiment of the present invention, a substrate having conductive regions may form the entire casing for the internal circuitry. Such a unibody device allows conductive pathways to be formed on any face of the substrate and complete eliminates the need for hermetically sealing a virtual wire assembly to a casing. Wires for the device may be deposited in the device using known techniques such as chemical vapor deposition. A unibody may be mounted inside a protective casing, such as a metal casing, as necessary when used in the various applications.

A virtual wire assembly of the present disclosure is easier to manufacture and requires less parts than prior art feedthrough assemblies. In addition, conductive pathways may be easily manufactured using automated processes. In one method of manufacturing the present invention, there a plurality of conductive regions are formed by doping regions of a substrate, with an n-type or p-type dopant, using known techniques, so that the conductive regions extend transversely through the substrate and are localized with respect to each other. Once the conductive regions are formed, at least one electrical contact may be connected to the conductive regions to form a conductive pathway.

Further, a virtual wire assembly according to the present invention may be of reduced size than the prior art which allows the virtual wire assembly to be used in miniature devices.

A virtual wire assembly of the present invention may be capable of being mass produced, requires less specialist and intensive labor resources, may be more accurate, more reliable, less complex, and less expensive while still maintaining a hermetical seal. This is because there is no need to provide punched or drilled holes through virtual wire assembly for inserting conductive pins, thereby leaving the structure of the substrate intact.

A virtual wire assembly of the present invention may be also capable of providing a more simplified connection between the hermetically enclosed electronic circuitry and any external components that are to be driven by such circuitry.

All documents, patents, journal articles and other materials cited in the present application are hereby incorporated by reference.

It will be appreciated by persons skilled in the art that numerous variations and/or modifications may be made to the invention as shown in the specific embodiments without departing from the spirit or scope of the invention as broadly described. In addition, while the primary embodiments address hearing implants, the teachings of the present invention are not limited to this area. The present embodiments are, therefore, to be considered in all respects as illustrative and not restrictive.

What is claimed is:

1. An assembly comprising:
a substantially electrically-nonconductive substrate having a plurality of hermetic feedthroughs comprising a first conductive region extending transversely through said substrate to form conductive surfaces on opposing sides of said substrate, wherein the respective first conductive regions are electrically isolated from one another, and wherein said substrate comprises a semiconductor device.

2. The assembly of claim 1, wherein said first conductive regions each are comprised of an n-type or a p-type doped semiconductor material.

3. The assembly of claim 1, wherein said assembly is integrated into a casing defining a hermetic enclosure, wherein said hermetic enclosure contains circuitry electrically connected to said accessible surface of at least one of said conductive regions, and wherein said accessible surface of each of said at least one conductive region is configured to be connected to an electrode lead.

4. The assembly of claim 1, wherein the first conductive region comprises a material that conducts electricity.

5. The assembly of claim 1, wherein said device further comprises an additional substrate having a plurality of second conductive regions, wherein said additional substrate is adjacent to said substrate such that said second conductive regions being substantially aligned with said first conductive regions.

6. The assembly of claim 5, wherein said substrate is attached to a casing on one side and attached to a casing extension on an opposite side, and wherein said casing and casing extension are joined together.

7. The assembly of claim 1, further comprising electrical contacts positioned at the opposing ends of said conductive regions.

8. The assembly of claim 7, wherein each of said electrical contacts is a pad for electrically connecting to a wire.

9. The assembly of claim 7, wherein said electrical contacts on at least one side of said substrate are in electrical communication with a ball grid array.

10. The assembly of claim 7, wherein each of said electrical contacts is a terminal for electrically connecting to a wire.

11. The assembly of claim 10, wherein each of said terminals is made of at least one material selected from the group consisting of gold; platinum; a eutectic alloy; and
an intrinsically electrically conductive polymeric material.

12. The assembly of claim 7, wherein said electrical contact is configured to be attached to a wire.

13. The assembly of claim 12, wherein at least part of said wire is located in a groove in said first conductive region.

14. The assembly of claim 12, wherein at least part of said wire is located in a depression in said substrate.

15. The assembly of claim 14, wherein said electrical contact is secured in said depression using a cold weld.

16. The assembly of claim 14, wherein said electrical contact is secured in said depression using mechanical tension.

17. An assembly comprising:
a casing; and
a substantially electrically-nonconductive first substrate integrated into the casing, wherein a combination of the first substrate and the casing is configured to be a hermetic enclosure, a plurality of conductive regions are formed within the first substrate, the first conductive regions extending from a first side of the first substrate to a second side of the first substrate and having conductive surfaces exposed at both sides of the first substrate, and each conductive region is electrically isolated from the other first conductive regions.

18. The assembly of claim 17, wherein the first substrate comprises a semiconductor device.

19. The assembly of claim 17, wherein each conductive region comprises one of an n-type or a p-type doped semiconductor material.

20. The assembly of claim 17 further comprising a ball grid array disposed within the casing, the ball grid array being in electrical communication with the exposed conductive surfaces on the second side of the first substrate.

21. The assembly of claim 17 further comprising a second substrate having a plurality of second conductive regions, wherein the second substrate is disposed adjacent to the first substrate such that the second conductive regions are substantially aligned with the first conductive regions.

22. The assembly of claim 17, wherein the plurality of conductive regions comprise material that conducts electricity.

23. The assembly of claim 17 further comprising a casing extension affixed to the casing and extending across the first substrate within the hermetic enclosure.

24. The assembly of claim 23, wherein the first substrate is affixed to the casing extension.

25. The assembly of claim 17 further comprising a plurality of conductive pads, each conductive pad being electrically connected to one of the exposed conductive surfaces.

26. The assembly of claim 25, wherein each conductive pad comprises an interconnect terminal.

27. The assembly of claim 25, wherein each conductive pad is made of at least one material selected from the group consisting of gold; platinum; a eutectic alloy; and an intrinsically electrically conductive polymeric material.

28. The assembly of claim 17, wherein at least one of the exposed conductive surfaces includes a depression adapted to receive a wire.

29. The assembly of claim 28, wherein the depression is adapted to secure the wire using a cold weld.

30. The assembly of claim 28, wherein the depression is adapted to secure the wire using mechanical tension.

* * * * *